United States Patent [19]

Wofford

[11] Patent Number: 5,542,003
[45] Date of Patent: Jul. 30, 1996

[54] METHOD FOR MAXIMIZING FIDELITY AND DYNAMIC RANGE FOR A REGION OF INTEREST WITHIN DIGITIZED MEDICAL IMAGE DISPLAY

[75] Inventor: Mark G. Wofford, Dallas, Tex.

[73] Assignee: Eastman Kodak, Rochester, N.Y.

[21] Appl. No.: 120,600

[22] Filed: Sep. 13, 1993

[51] Int. Cl.⁶ .................................................. G06F 159/00
[52] U.S. Cl. ........................... 382/132; 382/298; 395/139
[58] Field of Search ......................... 364/413.13, 413.22; 382/6, 132, 298, 299; 128/653.1; 395/101, 102, 139

[56] References Cited

U.S. PATENT DOCUMENTS

| | | | |
|---|---|---|---|
| 4,353,092 | 10/1982 | Bailey et al. | 358/160 |
| 5,305,204 | 4/1994 | Ohhashi | 364/413.13 |

OTHER PUBLICATIONS

Thurman Gillespy III, "Optimized Algorithms for Displaying 16-bit Gray Scale Images on 8-bit Computer Graphic Systems," *Journal of Digital Imaging*, vol. 6, No. 1 (Feb., 1993): 25–29.

Michael F. McNitt-Gray, Ricky K. Taira, Sandy L. Johnson, and Mahmood Razavi, "An Automatic Method for Enhancing the Display of Different Tissue Densities in Digital Chest Radiographs," *Journal of Digital Imaging*, vol. 6, No. 2 (May, 1993): 95–104.

*Primary Examiner*—Gail O. Hayes
*Assistant Examiner*—Joseph Thomas
*Attorney, Agent, or Firm*—Michael Roebuck

[57] ABSTRACT

A method and apparatus is presented in which a medical imagery workstation provides an end-user interface which when activated, windows and levels a whole image or a region of interest within the image utilizing the pixel values within a selection area. The method and apparatus customizes the pixel values when the entire image is selected before calculating the window and levels to produce a higher contrast, then redraws the entire image utilizing the newly calculated window and level values. The present invention provides a method and apparatus to enable an operator to define a region of interest, that when activated, the image is redrawn utilizing only the pixel values from the region of interest, maximizing the brightness and contrast of the selected.

8 Claims, 14 Drawing Sheets

Microfiche Appendix Included
(2 Microfiche, 69 Pages)

ILLUSTRATION OF REGION OF INTEREST

TO WINDOW AND LEVEL
SELECT THE ROI TOOL.

DRAG THE MOUSE
ACROSS THE AREA
YOU WANT TO SEE
AND RELEASE
THE BUTTON

OR

DOUBLE CLICK
ON THE IMAGE
AND THE WHOLE
IMAGE WILL
BE W/L
AUTOMAT-
ICALLY

← EXAMPLE OF
DRAGGING THE
MOUSE TO W/L
A SPECIFIC
AREA

METHOD FOR MAXIMIZING FIDELITY AND DYNAMIC RANGE FOR A REGION OF INTEREST WITHIN DIGITIZED MEDICAL IMAGE DISPLAY

BACKGROUND OF THE INVENTION

1. Field of the Invention

The present invention relates to the field of digital medical imagery and in particular to maximizing the contrast and brightness of an image transparently via a window-based graphic user interface tool that performs window and leveling functions based on a histogram of the raw image data in a region of interest presented at a medical imagery workstation.

2. Related Technology

Typical methods utilized to display and process diagnostic medical images for viewing at a workstation comprise the following: providing predefined default windowing and leveling values which are set up by a system manager; providing manual contrast and brightness control over the entire viewing area of a monitor using a pair of built-in dials; providing flip and rotate functions which are manually controlled through trackball/button selection of an on-screen icon; providing window/leveling values which are manually set by a mouse or trackball for individual windows wherein each window contains an image; providing continuous zoom within a window and a roam function to move the image within the window, or by stretching the window resulting in a magnified but not warped image; and providing user preference settings allowing the operator to predefine the window and level values.

Window and leveling parameters should be adaptable to different diagnostic tasks and to radiologist preferences. For example., the physician may desire to focus on a specific area within an image such as the lung area in a chest x-ray. Typically, selection &window and level values is performed by an apparatus or method which enables an operator to manually adjust window and level values within a particular area of interest. This manual method is however overly tedious and time consuming, especially when a user must select and readjust the window and level settings for each area of interest separately.

Moreover, in many instances, requirements for viewing medical imagery are time critical. Surgery may be necessary for immediate diagnosis. Time is of the essence in these circumstances, especially when human life is at stake. The pressure and associated tensions induced in medical diagnostic imagery technicians can be high. There is no room however for mistake or delay. It is thus necessary to have a rapid yet simple user interface available to technicians to enable users to rapidly manipulate medical imagery. Therefore, there is a need for a method and apparatus that rapidly yet transparently manipulates defined areas of an image and adjust window and level values to produce the highest possible fidelity and dynamic range, providing a superior display and analysis tool for the physician. Such a process would increase the speed at which medical diagnostic images could be made ready for delivery and diagnosis, as well as minimize human intervention and thereby reduce unnecessary operator errors.

SUMMARY OF THE INVENTION

The present invention comprises a method and apparatus designed to overcome the problems of the typical systems discussed above. The present invention provides an end-user interface known as a Region of Interest Window and Level tool (ROI tool) that helps to alleviate the problems of the typical systems discussed above. The present invention converts images to 8-bit display pixel depth values while minimizing the reduction in quality of the original input image. The present invention provides a method that provides improved windowing and leveling functions to a selected image. The present invention also provides an end user interface that, when selected, re-draws an image with improved fidelity and dynamic range based upon evaluation of a histogram for the pixel values within a region of interest.

The present invention provides a method which utilizes histogram data to eliminate anomalous pixel values. Thus, when the image is redrawn, the best contrast for the main body of data for the image is produced. The present invention provides an end-user interface (ROI tool) that enables a picture archival and communication system (PACS) to automatically calculate window and level values for an image utilizing only the pixel values within a user-defined rectangle. The present invention determines improved window and level values for the image pixels within the region of interest, without regard to the pixel values for the remainder of the image outside of the region of interest.

The present invention provides a method and apparatus for displaying a medical diagnostic image comprising: transforming a physical image of a patient into a digital representation of pixels; displaying the imagery on a workstation; selecting an area of the image displayed on the workstation; calculating a histogram for the selected area of the image representing the number of occurrences of each pixel magnitude which exists in selected area of the image; determining the total number of occurrences of all pixel magnitudes represented in the selected area of the image; determining a number N equal to a selected percentage of the total number of occurrences of all pixel magnitudes represented in the selected area of the image; summing the number of occurrences for each pixel magnitude starting with the smallest magnitude represented in the histogram and preceding to the next smallest magnitude represented in the histogram until the total number of occurrences is greater than or equal to N; setting a Variable MIN equal to the magnitude of the pixel value at which the count of occurrences of the smallest pixels in the histogram is greater than or equal to N; summing the number of occurrences for each pixel magnitude starting with the largest magnitude represented in the histogram and preceding to the next largest magnitude represented in the histogram until the total number of occurrences is greater than or equal to N; setting a variable MAX equal to the magnitude of the pixel value at which the count of such occurrences of the largest magnitude pixels is greater than or equal to N; and calculating a window value and level value utilizing a set of pixel values represented by the variables MIN and MAX.

The present invention also provides a method and apparatus wherein the percentage selected is 1 percent.

The present invention also provides a method and apparatus further comprising: providing a user interface to enable a user to select a region of interest within an image for calculation of new window and level values.

The present invention also provides a method and apparatus for displaying a medical diagnostic image comprising: transforming a physical image of a patient into a digital representation of pixels; displaying the imagery on a workstation; selecting an area of the image displayed on the workstation; calculating a window value and level value utilizing a set of minimum and maximum pixel values existing within the selected area of the displayed image.

The present invention also provides a method and apparatus further comprising: calculating a histogram for the selected area of the image representing the number of occurrences of each pixel magnitude which exists in selected area of the image.

The present invention also provides a method and apparatus further comprising: determining the total number of occurrences of all pixel magnitudes represented in the selected area of the image; determining a number N equal to a selected percentage of the total number of occurrences of all pixel magnitudes represented in the selected area of the image; summing the number of occurrences for each pixel magnitude starting with the smallest magnitude represented in the histogram and preceding to the next smallest magnitude represented in the histogram until the total number of occurrences is greater than or equal to N; setting a variable MIN equal to the magnitude of the pixel value at which the count of occurrences of the smallest pixels in the histogram is greater than or equal to N; summing the number of occurrences for each pixel magnitude starting with the largest magnitude represented in the histogram and preceding to the next largest magnitude represented in the histogram until the total number of occurrences is greater than or equal to N; and setting a variable MAX equal to the magnitude of the pixel value at which the count of such occurrences of the largest magnitude pixels is greater than or equal to N.

The present invention also provides a method and apparatus further comprising: selecting less than all the pixel values within the selected area; and calculating a histogram based on the selected for the selected area of the image representing the number of occurrences of each pixel magnitude which exists in selected area of the image.

The present invention also provides a method and apparatus further comprising: determining the total number of occurrences of all pixel magnitudes represented in the selected area of the image; determining a number N equal to a selected percentage of the total number of occurrences of all pixel magnitudes represented in the selected area of the image; summing the number of occurrences for each pixel magnitude starting with the smallest magnitude represented in the histogram and preceding to the next smallest magnitude represented in the histogram until the total number of occurrences is greater than or equal to N; setting a variable MIN equal to the magnitude of the pixel value at which the count of occurrences of the smallest pixels in the histogram is greater than or equal to N; summing the number of occurrences for each pixel magnitude starting with the largest magnitude represented in the histogram and preceding to the next largest magnitude represented in the histogram until the total number of occurrences is greater than or equal to N; and setting a variable MAX equal to the magnitude of the pixel value at which the count of such occurrences of the largest magnitude pixels is greater than or equal to N.

DETAILED DESCRIPTION OF A PREFERRED EMBODIMENT OF THE PRESENT INVENTION

The present invention will be further clarified by consideration of the following examples, which are intended to be exemplary of the invention and are not intended to limit the scope of the claimed invention.

Overview of the System Environment

Figure 3:
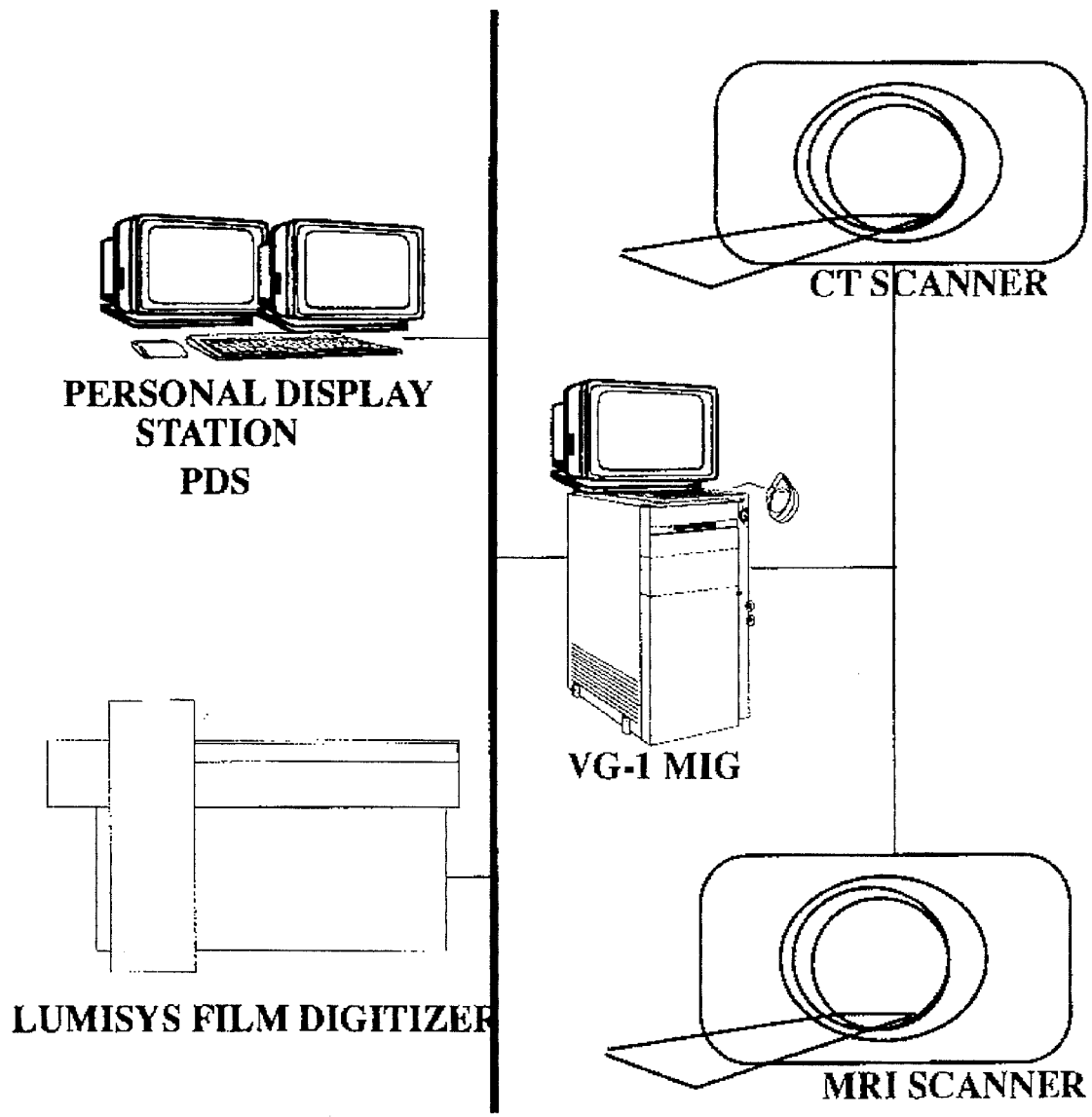
FIG. 3 is an illustration of the present example of a preferred embodiment of the present invention showing a Picture Archival and Communication Systems (PACS).
Figure 4:
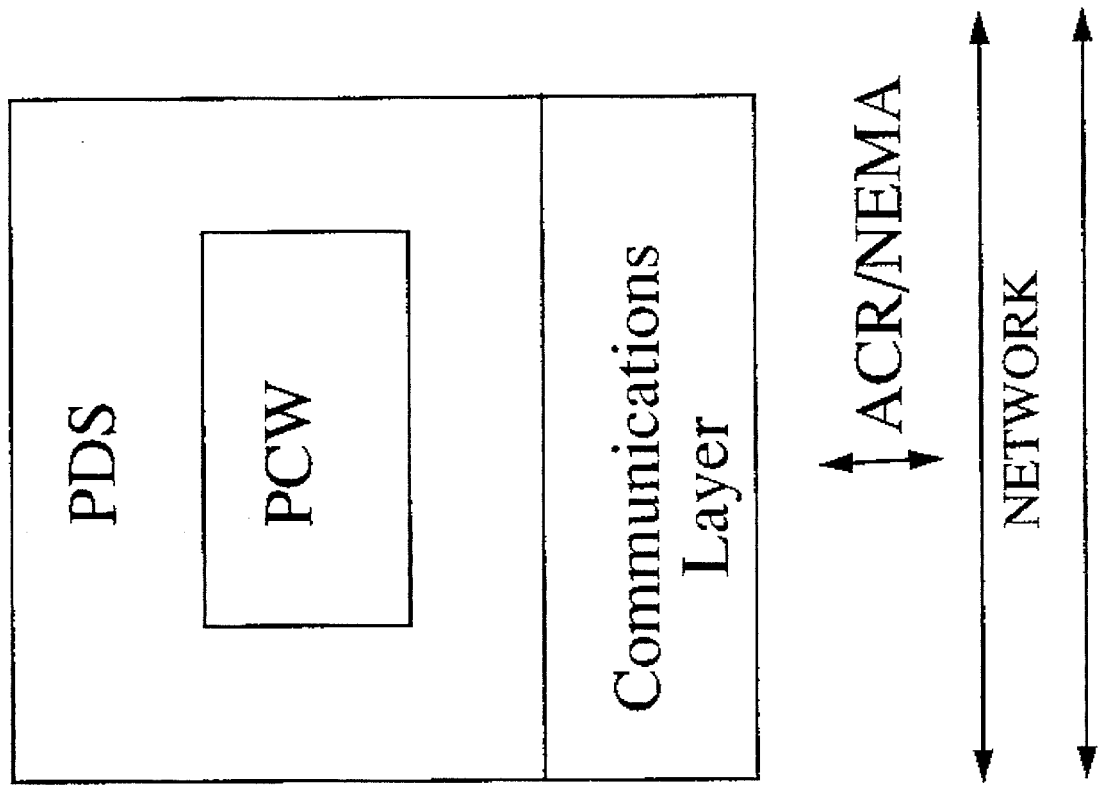
FIG. 4 is an illustration of the present example of a preferred embodiment of the present invention depicting a PDS connection to a network.

The present example of a preferred embodiment of the present invention operates as an addition to a Picture Archival and Communication System (PACS) as shown in FIG. 3. The present invention preferably operates as an integral part of the Personal Display System (PDS) as shown in FIG. 4, utilizing the PDS software provided by Vortech Data, Inc. of Richardson, Tex. The industry has cooperated to produce a set of standard protocols. The preferred embodiment utilizes the American College of Radiology-National Electrical Manufacturers Association referred to as the ACR-NEMA 300-1988 language. ACR-NEMA is more properly referred to as a communication protocol or format. This standard comprises a standard hardware interface, a minimum set of software commands, and a communication protocol.

The preferred embodiment of the present invention resides within the PDS. The present invention provides a palette-based user interface tool that enables the end user to select a Region of Interest (ROI) tool. The present invention transparently performs window and level functions in real time on the selected area of an image or the entire image within a displayed medical diagnostic image. There are a number of functions called upon to support the ROI in the present example of a preferred embodiment.

In the present example of a preferred embodiment, there are six primary functions that are provided by use of Biofunctions to ROI, depending on the action desired. The two primary functions are provided to calculate a histogram and to calculate window and leveling values. The remaining functions open a histogram window, draw a histogram window, calculate the minimum and calculate the maximum pixel values at full resolution of the image. These latter four functions are performed once and are saved along with the image data to be utilized later as needed. "Clicking" the mouse on an image window, processing part of the window containing the image, and activating the currently selected tool, are handled at a higher level in the PDS software. Once the ROI tool of the present invention is activated, the user may select an area for processing by clicking in the image area, and the ROI functions are automatically performed.

Figure 5:
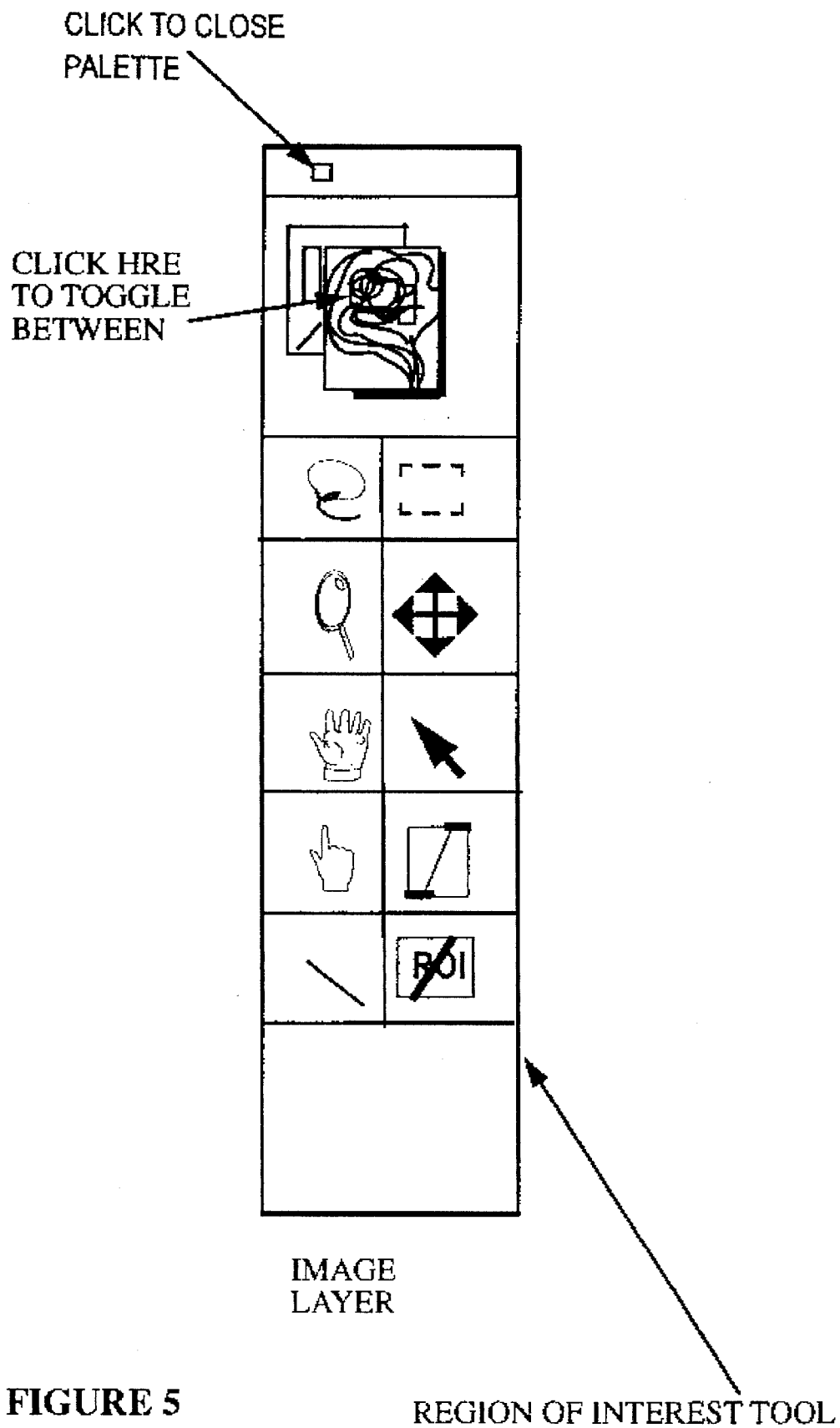
FIG. 5 is an illustration of the present example of a preferred embodiment showing a tool palette, and the Region of Interest, ROI tool.
Figure 6:
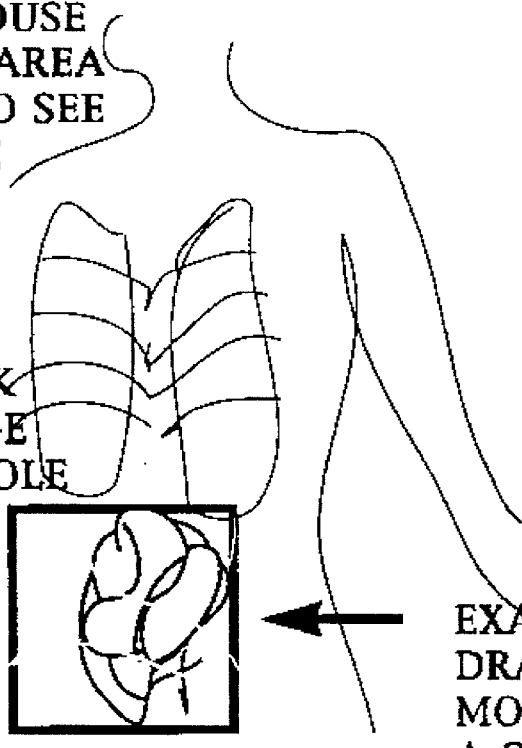
FIG. 6 is an illustration of an image that has been redrawn utilizing the values within the region of interest to determine the optimum window and level values.

In a preferred embodiment of the present invention, oftentimes an image is received with undesirable window and leveling values or without window and leveling values. As shown in FIG. 5, the operator may double click on a displayed image to select the entire image and pixel values from the entire image will be utilized to calculate window and level values to provide improved fidelity and dynamic range at the display. As shown in FIG. 6, when the operator selects the ROI functions and drags the mouse device across a specific region &interest, a "rubber-banded" rectangle appears over the selected area until the mouse button is released. The parameters of this rectangle are considered as the boundaries of the region of interest. The rectangle disappears when the mouse button is released. The ROI functions determines the minimum and maximum pixel values within the region of interest based on the raw image data pixel values. The present invention utilizes these minimum and maximum pixel values for the region of interest tool which calculates new window and level values and redraws that portion of the image within the rectangle with the improved fidelity and dynamic range, as shown in FIG. 6.

The present example of a preferred embodiment of the present invention utilizes histogram analysis to perform windowing and leveling functions on images in the ROI process. The present example of a preferred embodiment of the present invention provides a unique interface. No other system known to the inventor enables the end user to automatically determine improved window and level values for a region of interest utilizing such a histogram-based analysis.

Figure 2A:
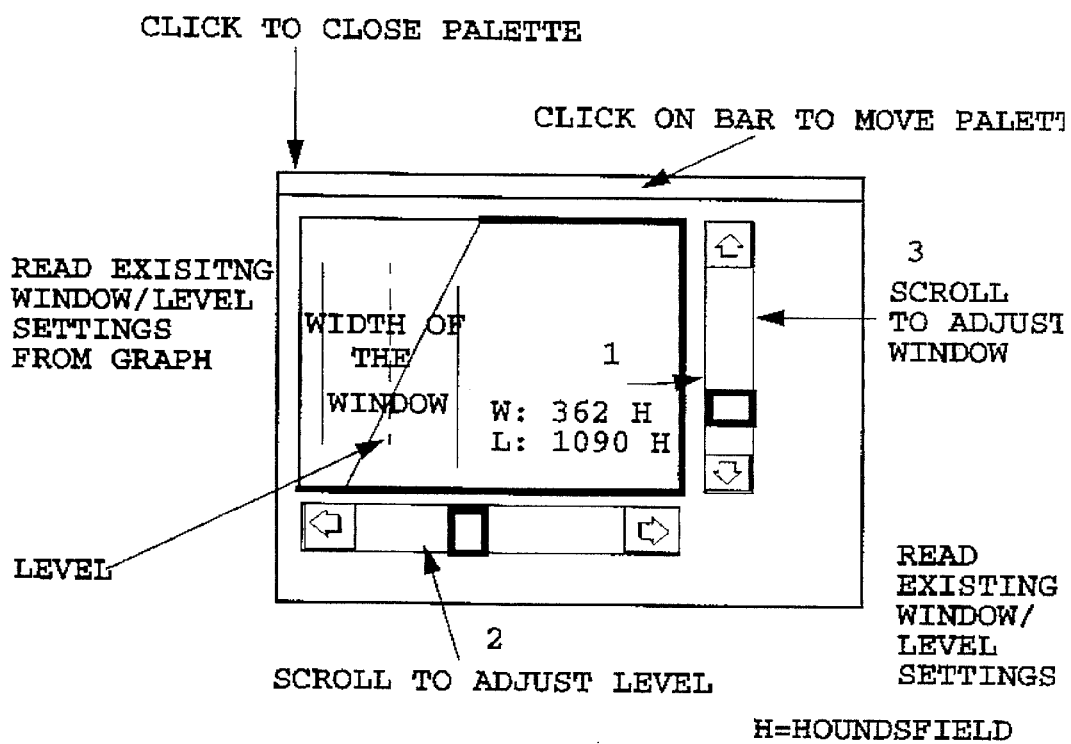
FIGS. 2A and 2B are illustrations of a typical manual method utilized to set the window and level values from a menu based program.
Figure 2B:
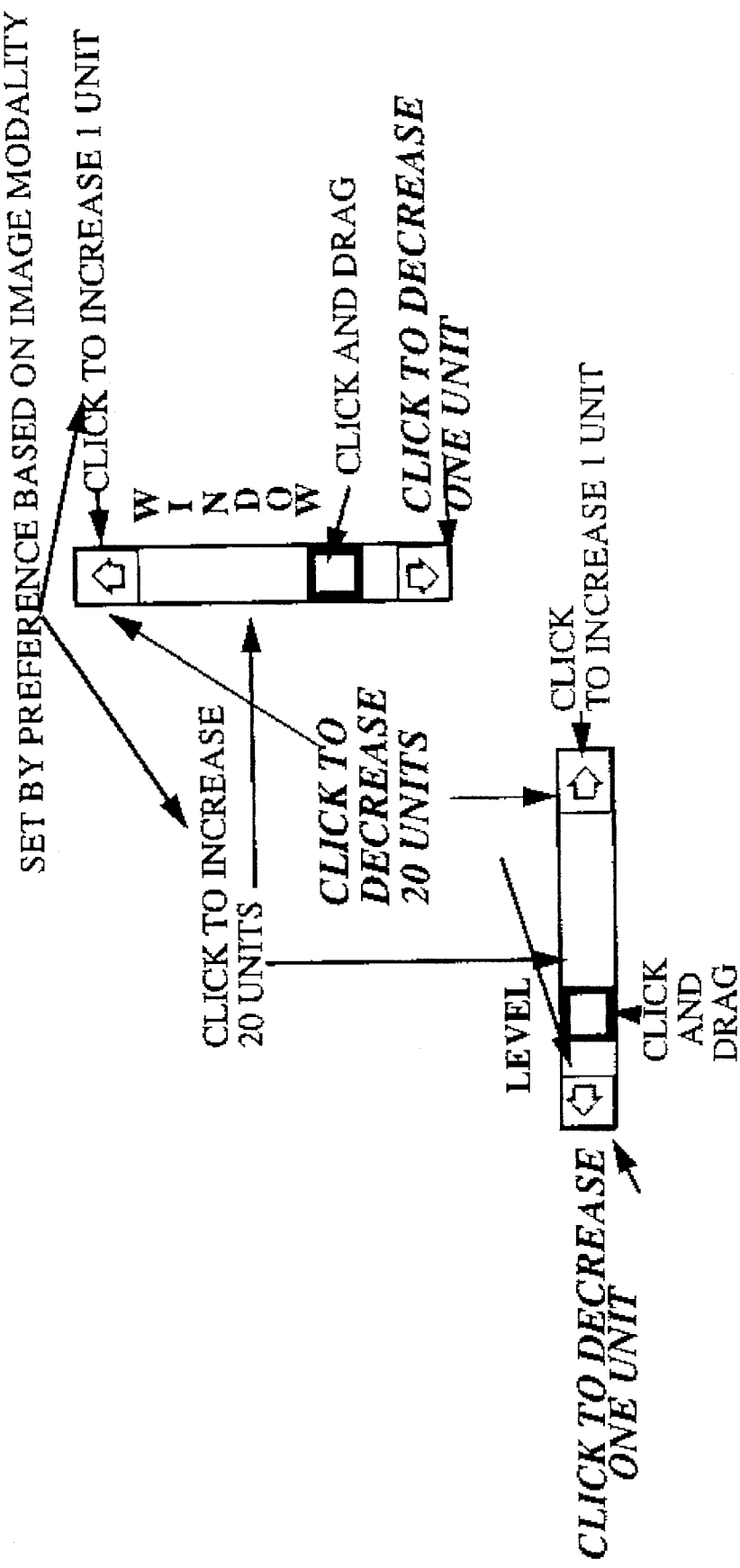

In the present example of a preferred embodiment, the PDS enables an end-user to step through a series of menu-driven programs to select an image, or a series of images for viewing. The selected images may or may not have window and level values assigned to them. If an image has been previously viewed, the window and level values that were stored in the database image structure are presented along with the image. If the image has not been previously displayed, the window and level values for the image may be predefined by the source modality. If a preference function is available, predefined values may be assigned to the image according to the preference values, as shown in FIG. 2. Otherwise, when the image is displayed, absent proper window and level values in the image may appear with little or no contrast. The end-user can manually adjust window and level values for the image to obtain the improved fidelity, or the user may automatically improve fidelity and dynamic range by use of the present invention. The present invention will automatically adjust the image to attain new windowing and leveling values to provide improved fidelity and dynamic range at the display.

In a preferred embodiment, the present invention performs two primary actions. First, with the ROI tool of the present invention selected, the end user selects an image. The present invention (1) calculates window and level values for the entire image, utilizing a unique customized process which is automatic and transparent to the end-user or (2) if the end-user utilizes the mouse to create a rectangle defining a specific region of interest, the present example of a preferred embodiment of the present invention redraws the entire image utilizing only the minimum and maximum pixel values that exist within the defined rectangle (ROI to compute new windowing and leveling values, while preferably ignoring the pixel values for the rest of the image in calculating window and level values.

The present example of a preferred embodiment of the present invention provides one main function and two sub-functions. This main function is responsible for determining what action is required, processing the image, calling histogram functions for needed information, such as calculation of new pixel values, drawing the window and updating the image structure with the new pixel values. After the entire image or a specific region of interest of a image has been redrawn, the new window and level values are passed to the PDS database image structure and stored in association with that image.

The ROI function calculates the width and height of the rectangle defining the region of interest that is to be windowed and leveled. It passes a pointer to this information to the histogram function. The histogram function utilizes these parameters to determine the minimum and maximum pixel values within the rectangle defining the region of interest. The pixel values may be subsampled that is, less than all pixel values selected to reduce the amount of data. The new histogram values are then passed to the ROI function and the second ROI sub-routine, "calculate_WL_values," calculates new windowing and leveling values for the ROI area based upon the new calculated histogram values, and redraws the image utilizing the new window and level values.

The hardware environment of the present invention is preferably a PDS. In a preferred embodiment, PDS utilizes a Macintosh II family of workstations as the host computer. In a preferred embodiment of the present invention, the software utilized by the present invention resides along with the Macintosh operating system 7 on the host computer. Both hardware and software requirements are discussed in detail in the following sections.

Many modern hospitals or treatment centers are geographically distributed, and thus typically utilize many different types of communication networks. Hospital radiology centers typically receive images from a multitude of diverse modalities and retransmit these images to various viewing devices such as a PDS, as shown in FIG. 3. A preferred embodiment of the present invention utilizes standard protocol ACR-NEMA format for image distribution. A preferred embodiment abstracts the details of image formatting protocols, thus hiding the details from the operator, yet enables the user to customize ACR-NEMA messages for recurring jobs and emergencies.

As shown in FIG. 3, a Medical Imaging Gateway (MIG) provides a platform for the transmission of diagnostic quality images at high speeds between different locations. The MIG serves as an interface between sources of medical images (the source image generators), image display workstations, and imaging networks. The transmission medium may be satellite-based communications over the Vortech Image Transmission Network (ITN), dedicated fiber optic lines, or any other form of data transmission suitable for diagnostic medical imagery.

The MIG software supports communications with Imaging Equipment (IE) using the ACR-NEMA 1.0/2.0 protocol via a TCP/IP connection to the IE. The MIG software enables IE devices to communicate over a ITN utilizing a standard protocol. The software process that provides this interface capability is called VPAT.

Figure 13:
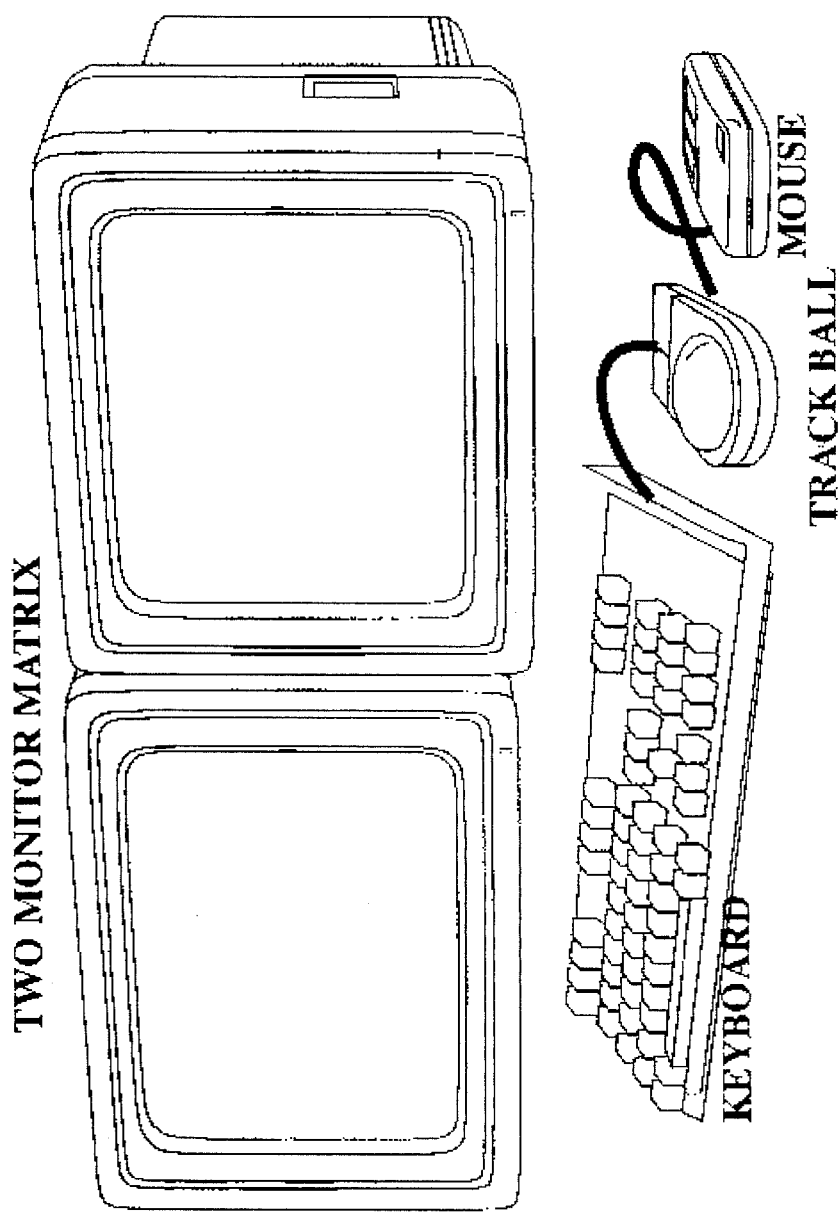
FIG. 13 is a drawing of a PDS workstation utilized in the present example of a preferred embodiment.

The PDS comprises a series of image display workstations based upon a Macintosh computer, as shown in FIG. 13. PDS provides access to diagnostic quality digital images from numerous modality devices: e.g., digitized film radiographs, optical disk archives or computed radiography. PDS may be connected to other equipments throughout a hospital, as well as to another clinical site located miles away.

Figure 11:
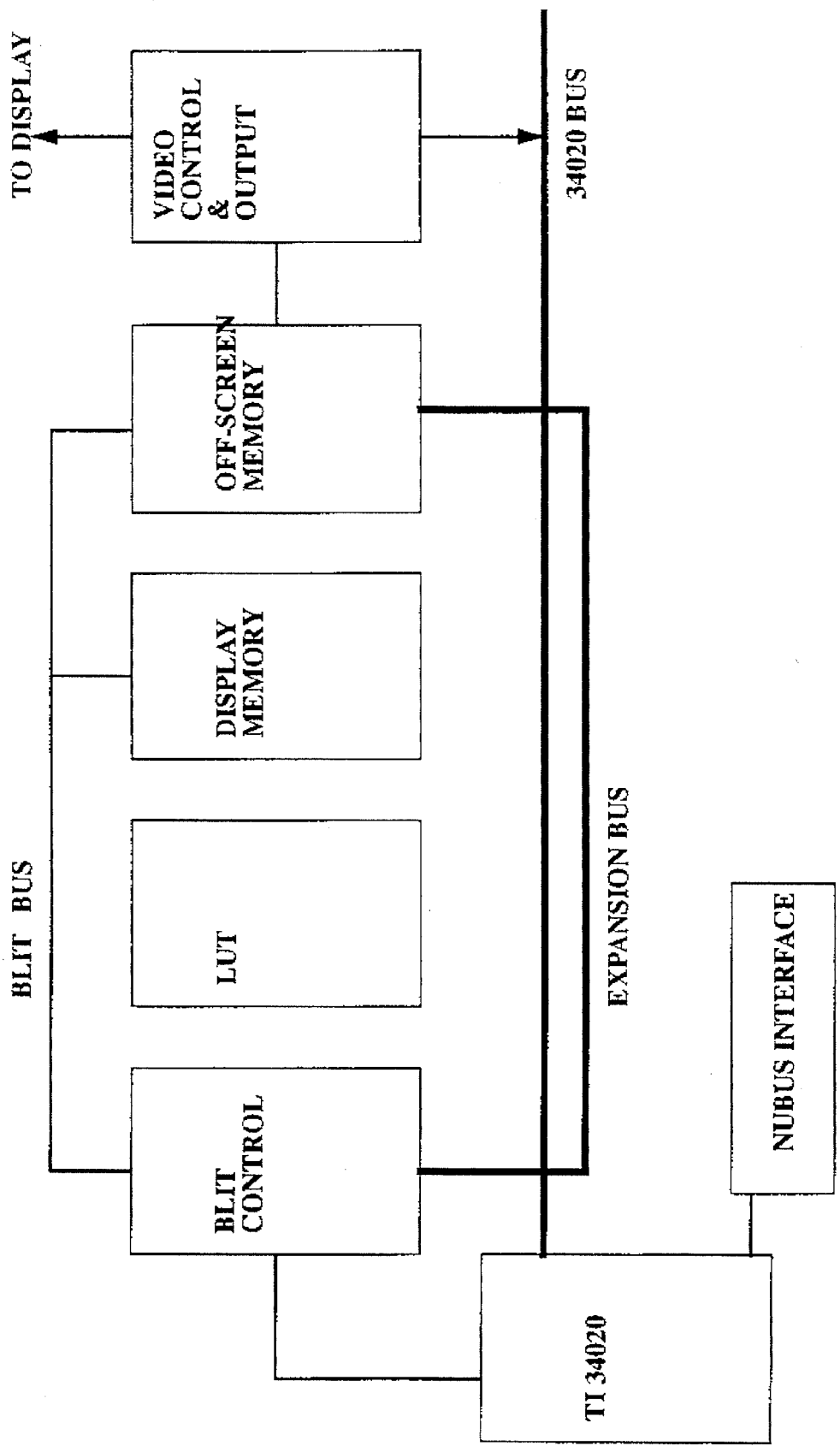
FIG. 11 is an illustration of the present example of a dome image display board in a preferred embodiment.

A high-performance Ethernet controller provides basic connectivity to the medical information network. In the present example of a preferred embodiment, the present invention utilizes a Dome Macintosh imaging display board, as shown in FIG. 11, for each dedicated display in a PDS. The Dome card is preferably a 10 Mhz 32-bit Texas Instruments TMS 34020-based specialized image processor. In a preferred embodiment of the present invention, the ROI image presentation features include: display of diagnostic images positioned inside of windows utilizing typical industry standard window creation and positional manipulation operations, and image organization as it pertains to the appearance and positional manipulation functions available within each window.

A preferred embodiment provides a graphic user interface to enable an operator to arrange imagery and compose new images. Annotation functions are provided by a larger application in the PDS tool palette which provides the capability to write text and draw lines, circles, or rectangles over imagery. Annotations can be utilized for outlining or highlighting original imagery as it is displayed at a workstation. In a preferred embodiment, PDS functions are available to modify the characteristics and properties of the original imagery as well.

In a preferred embodiment, a graphic user interface provides a dialog box, implemented in PDS, which directs an operator to sequence through a patient menu hierarchy (e.g., patient-study-series-acquisition-images) to select patient image data. Dialog boxes are utilized to query the operator for input, when necessary or desirable.

In a preferred embodiment, system supplied default values are provided for composition and printing parameters. The operator may change these default parameter values via input through a dialog box. These default parameter settings are initialized each time the present invention is restarted. Default settings are applied to the graphics workstation display parameters during imagery composition and display.

In a preferred embodiment, a pointer device or a trackball is a primary means of directing activity on the display workstation. These devices may be utilized for pull-down menu selections, image selection and positioning, and also for drawing geometric shapes such as lines, rectangles, and circles as overlays on a displayed image. These devices enable the operator to select, point, or drag an object by clicking a control button, move objects between windows, or choose an action to apply to some selected object.

Figure 9:
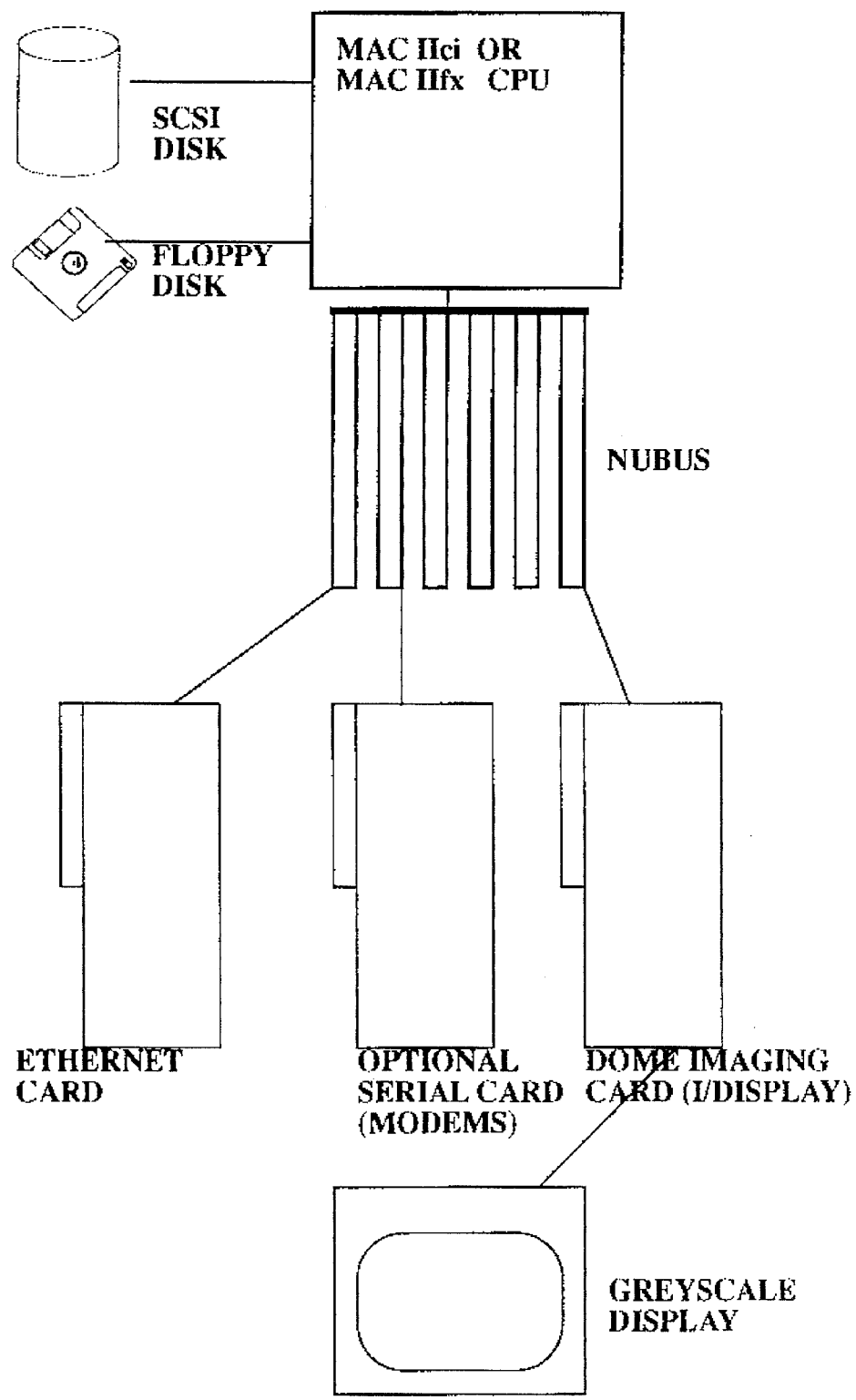
FIG. 9 is an illustration of the present example of a hardware system in a preferred embodiment.

FIG. 9 illustrates a block diagram of a video image display system incorporating a hardware environment in which the present example of a preferred embodiment of the present invention may reside. In a preferred embodiment, this hardware environment is the PDS manufactured by Vortech Data, Inc. of Richardson, Tex.

The MACII family of work stations is utilized as the host computer for application programs. MACII architecture lends itself to most image manipulation and display applications, given its high performance (1.5 to 20 million instructions per second (MIPS) depending on the model) and open design (NuBus).

Still referring to FIG. 9, the major hardware components of a preferred hardware environment are illustrated as follows: a Macintosh II fx or ci computer 10, a small computer system interface (scsi) hard disk drive 11, a floppy disk drive 12, an Ethernet interface card 16, an imaging processor card 17, a Greyscale video display 18, a mouse or trackball, and an optional serial card 19.

In a preferred embodiment of the present invention, the system bus 13 is preferably a NuBus. A high-performance ethernet controller 16 provides the basic connectivity within the Medical Imaging Gateway (MIG) for the reception of image data.

A preferred embodiment utilizes a Dome Macintosh Imaging Display Board 17 for each dedicated display. The Dome card is preferably a 10 Mhz, 32-bit, TI TMS 34020-based specialized image processor. A preferred embodiment supports up to 6 high-resolution displays 18.

Software

The software for a preferred embodiment is contained in the Software Microfiche Appendix. The software environment, in the present example of a preferred embodiment, is the Macintosh operating system which provides a host software environment for software applications running on the Macintosh-based PDS workstations. PDS workstation operators view and edit diagnostic images. A preferred embodiment comprises a local database which enables user accessibility and efficient organization of image and report files made available to the user.

Figure 7:
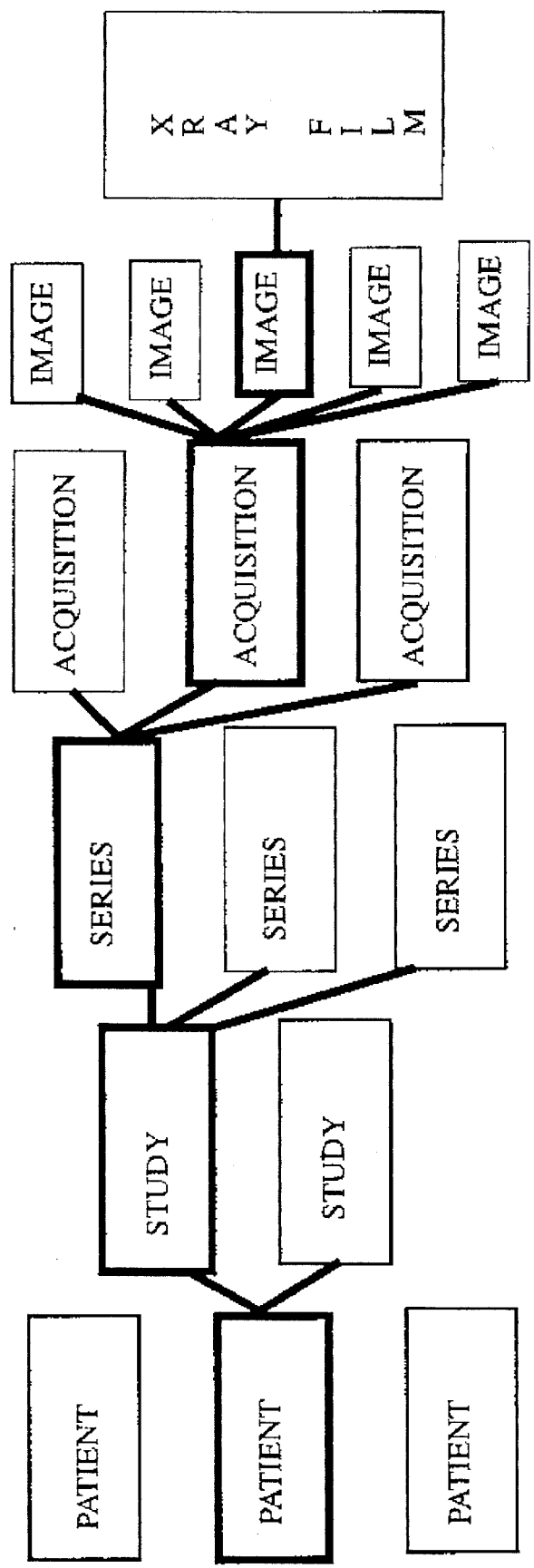
FIG. 7 is a drawing of the PDS database structure hierarchy in the present example of a preferred embodiment of the present invention.

In a preferred embodiment of the present invention, the software comprises a configuration file, header files, global variables, data structures, and application modules. FIG. 7 depicts a typical PDS configuration path. In a preferred embodiment, operations are performed on window-oriented data structures which conform to specifications for the toolbox and palette implementation. Pick and point operations are accomplished utilizing a mouse, trackball, lightpen or other user input device.

Database

In a preferred embodiment of the present invention, the PDS local database is a standard database that utilizes "db_vista" software. PDS contains codes which comprise a database interface with the ability to access and utilize the standard "db_vista" database.

The PDS database keeps track of the patients and their associated images. Image structures residing in the PDS database are mapped to an ACR-NEMA header. There are many translation routines that translate between the two, the data base and ACR-NEMA messages. When patient information is altered in the database, the PDS database updates the ACR-NEMA header information. The PDS database supports a structure hierarchy, as shown in FIG. 7.

User-Interface

In a preferred embodiment of the present invention the user interacts directly via a pointer and keyboard inputs. The top level PDS event handler responds to user input. PDS provides a mechanism which enables a module to define a single function which may be called to handle an event, instead of relying on the PDS event handler. The value returned from the PDS event handler is interpreted by the PDS to determine if PDS should process the event or allow another function to process the event.

A preferred embodiment utilizes the popular desktop metaphor interface implemented on the Macintosh computer, manufactured by Apple Computer, Inc. Many work place extensions are based upon this metaphor. Others implement IBM's OS/2 Presentation Manager or Microsoft's Windows. The widespread popularity of this interface is partially attributable to its ease off-earning and simplicity of communicating with complex applications which run on these new graphics user-interface platforms.

Figure 8:
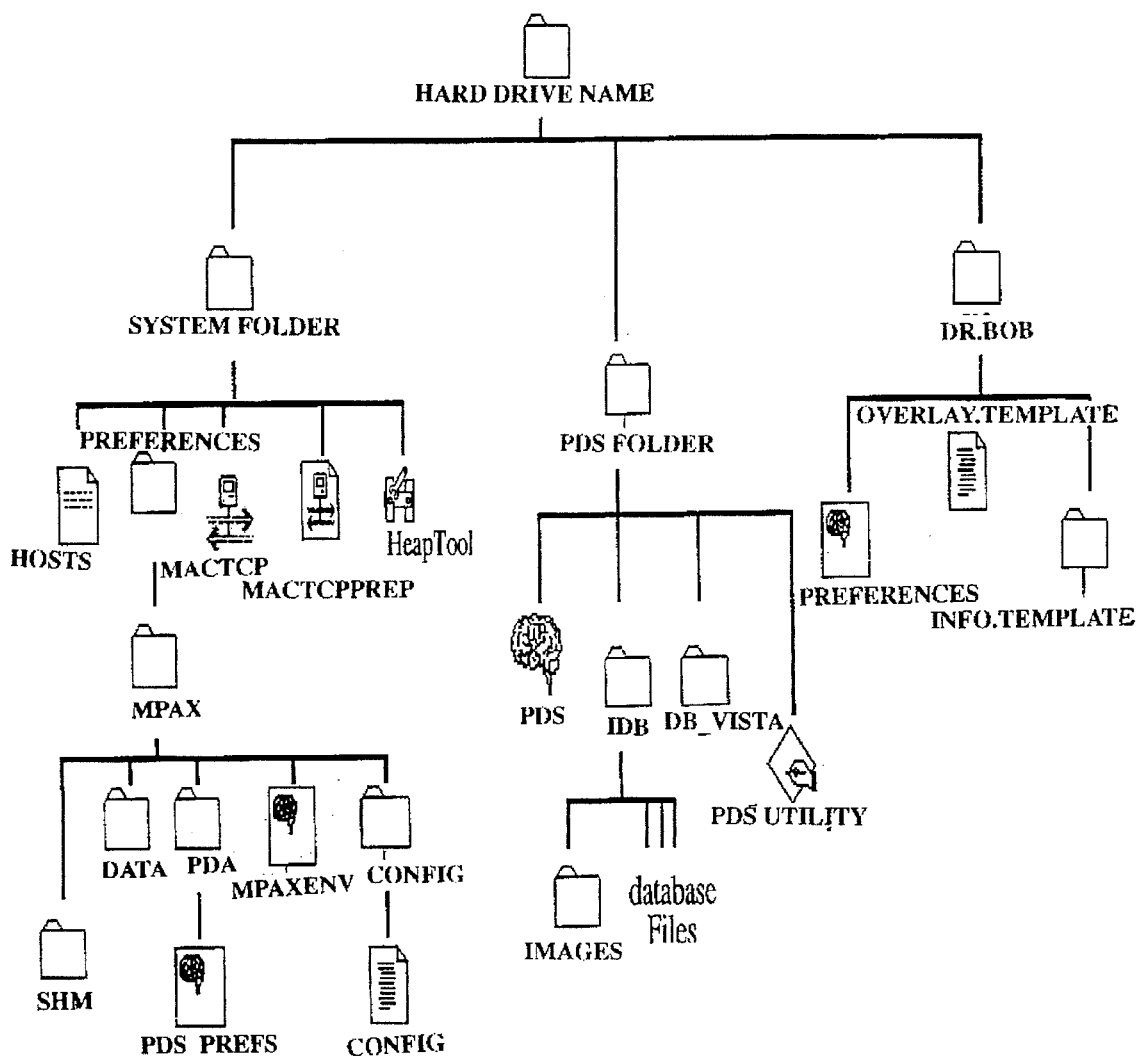
FIG. 8 is an illustration of the present example of a configuration path in a preferred embodiment.

In a preferred embodiment of the present invention an operator's input is solicited within an open window, via a special type of window referred to as a dialog box. A dialog box can be opened or created inside of another active window. Dialog boxes are utilized in window-oriented interactive applications to solicit additional information from the workstation operator whenever an operator action or input is desired FIG. 8 illustrates a PDS configuration path.

Graphics Applications

Figure 1:
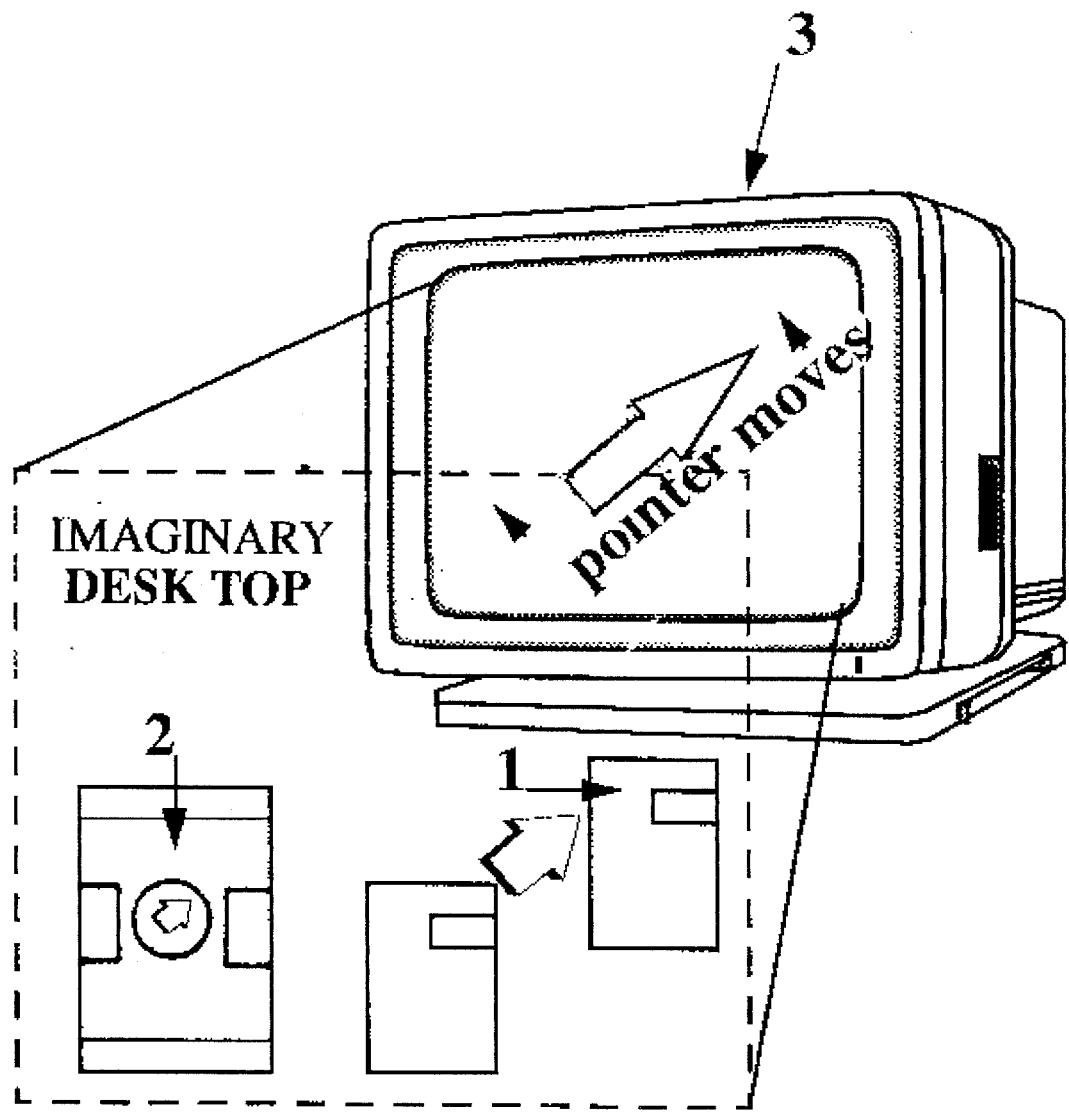
FIG. 1 is an illustration of the present example of a preferred embodiment of the present invention illustrating the trackball and mouse devices utilized to manipulate an image.

In a preferred embodiment, the present invention runs as a graphics application on a host computer. In a preferred embodiment, the Macintosh host computer generates update image events in response to user inputs. A user initiates an input, typically via a mouse or track ball attached to the host computer as shown in FIG. 1, to request an application to send image data to a window to be displayed on the computer display screen. The present invention receives an update image event and prepares the image data for processing by an external dedicated hardware graphics controller. Once the present invention has prepared the image data, it sends a command directly to the graphics controller. The graphics controller then copies the image data into display memory so that the imagery appears in the window on the computer display screen as shown in FIG. 11.

Region of Interest

In a preferred embodiment of the present invention, the Region of Interest process provides an end-user interface which enables a PDS user to automatically and transparently recalculate improved windowing and leveling values for an image thereby producing the best possible contrast and fidelity at a display such as the PDS. The present invention also provides an end-user interface that enables the operator to define a region of interest (ROI) within an image. When the image is redrawn, the detail and contrast in the ROI is improved while image detail outside of the ROI may be undetermined.

In a preferred embodiment of the present invention, images are received by the PDS from a source device and stored in a local database. The elements of information associated with the image are mapped from the ACR-NEMA header and sent along with the image to the database to be utilized by different functions, including the present invention. The structure in the database that handles and stores the image parameters and data is referred to as the "image structure." When an image, or an area within an image is manipulated, changed, or redefined, the image structure is updated. Every function that deals with windows or an image utilizes this image structure data.

In a preferred embodiment of the present invention, when the List Patients or Open a File functions are invoked, the present example of a preferred embodiment lists the groups of images available for viewing and processing at the workstation. In a preferred embodiment, there are 5 tiers or levels: Patient, Study, Series, Acquisition and Image as shown in FIG. 7. The user can quickly move between levels to identify an image for viewing.

In a preferred embodiment, an image tool palette is provided that displays the tools that perform various actions. The present invention is located and displayed for use in this tool palette as shown in FIG. 5. In the present example of a preferred embodiment, the user activates the present invention, selects the ROI tool from the tool palette, then double clicks on the image, or moves the mouse to the region of interest, holds down the mouse button, and a rubber-banded rectangle appears as the user drags the mouse across the area the user wants to window and level. When the mouse button is released, the ROI is defined and the rectangle disappears.

A preferred embodiment utilizes histogram functions which calculates the number of occurrences of each pixel value which exists within an entire image or only within the rectangle. The histogram values are passed back to the present invention to compute new windowing and leveling values that produce the improved contrast for the entire image, or for the specific area of the image defined within the rectangle. The present invention updates the image structure, and redraws the entire image utilizing the new window and level values. If a region of interest was defined, when the image is redrawn, the detail and contrast within the ROI will be improved, while image detail outside of the ROI may be undetermined.

The present invention updates the image structure in the PDS database when it changes an image. The new windowing and leveling values will be updated from the image structure in the ACR-NEMA header to reflect the new values.

Processing

Figure 10:
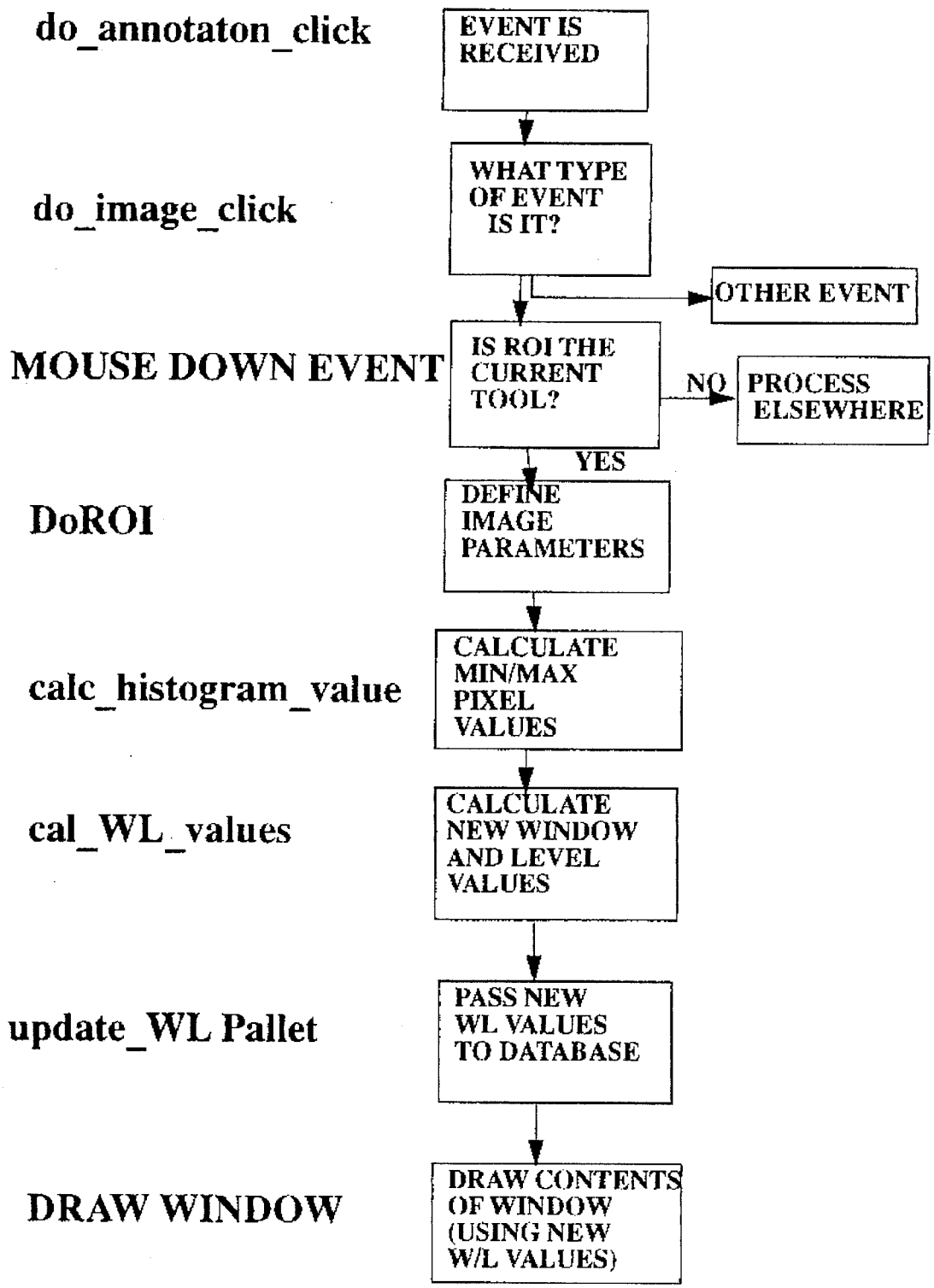
FIG. 10 is an illustration of an event flow path for a preferred embodiment of the present invention.
Figure 12:
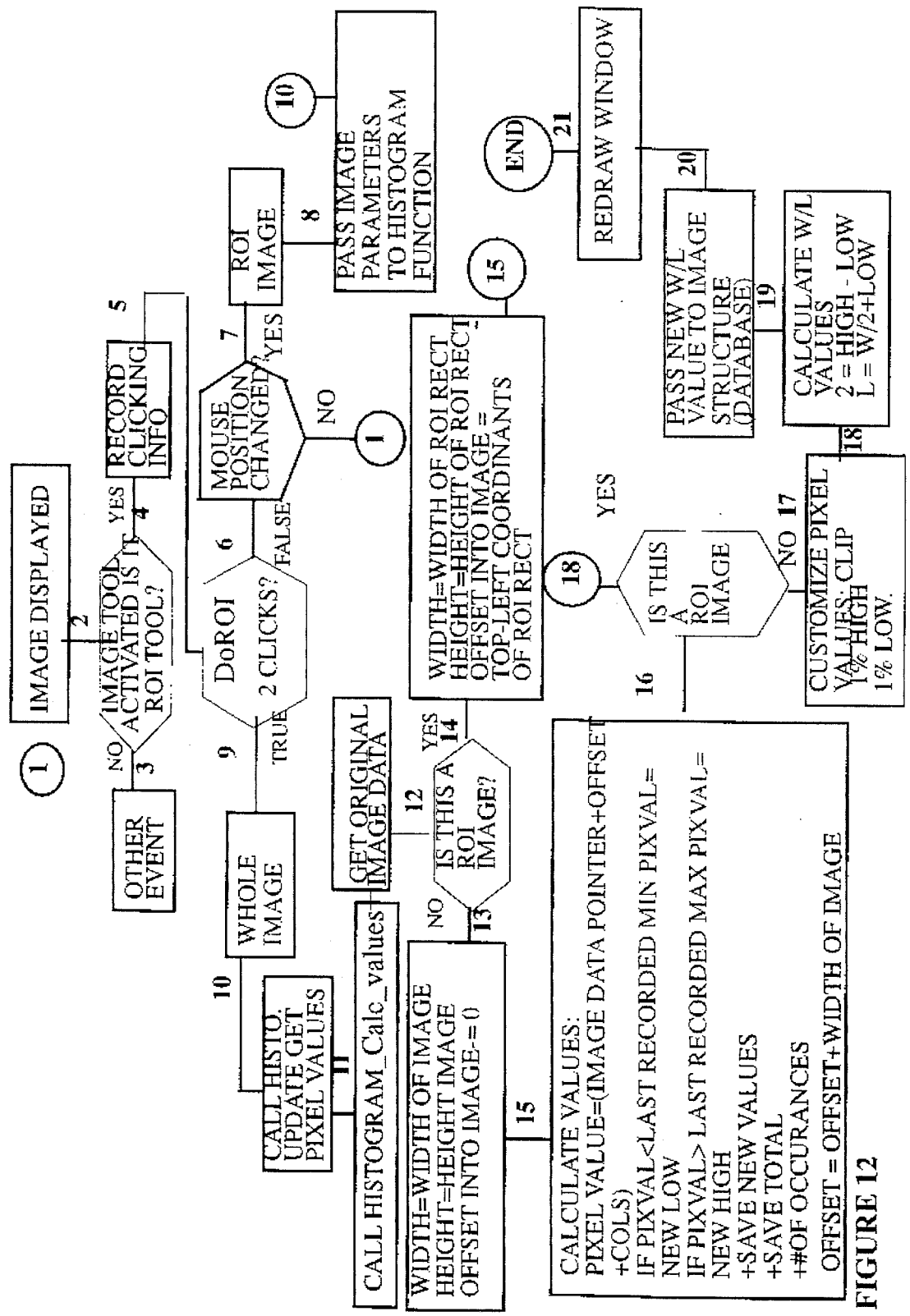
FIG. 12 is a Data Flowchart for the software utilized in the present example of a preferred embodiment of the present invention.

FIG. 10 illustrates an Event Handling Flowpath which comprises the steps performed in a preferred embodiment of the present invention. FIG. 12 illustrates a flowchart which comprises the details of the steps performed in a preferred embodiment. Referring to FIG. 12, an image is displayed (1) and the ROI tool is selected, the PDS "do_annotation_click" routine verifies the user has clicked on the tool palette, and highlights the ROI tool (2). The PDS routine, "do_Image_click" counts how many clicks were performed after the tool was selected, the position of the pointer and the time of the action (4).

A preferred embodiment passes the number of clicks, pointer position and time parameters (5) to the present invention to determine what task needs to be performed. There are two functions that are performed in the present invention after the user selects the ROI tool. One, if the user double clicks on the content (image), the present invention redraws the entire image with new window and level values calculated based upon the minimum and maximum pixel values which exist within the entire image (9). Two, if the user creates a rectangle defining a specific region of interest and the present invention redraws the entire image, but with the window and level values based only on the minimum and maximum pixel values within the region of interest (6).

In a preferred embodiment, if a double click is recorded, the present invention calls the "update_histogram" routine. This routine retrieves the current minimum and maximum pixel values for that entire image (10). The histogram routine passes the stored histogram values for the image to the "calc_Histogram_Values" routine to determine the new minimum and maximum pixel values based on the original image data (11).

To eliminate aberrant pixel values, and improve the dynamic range of the display over the range pixel values for the majority of the data, a preferred embodiment of the present invention customizes the histogram pixel values that it receives. In a preferred embodiment, the present invention sums up the total number of pixels which exist by adding or summing all occurrences of all magnitudes represented by the histogram. The present invention then calculates 1% of pixels occurring within the image data, and loops through the histogram data to recalculate new minimum pixel values greater than 1%, and new maximum pixel values less than 99% of the image data. Removing 1% of the pixels from the high and the low end of the image pixel values produces improved fidelity and dynamic range for display of the image (17).

The new histogram values are passed to the present inventions calculation routine, "Cal_WL_Values." "Cal_WL_Values" determines the difference between the maximum pixel value and the minimum pixel value which becomes the new window width. To calculate the level, the Window width is divided by 2 plus the minimum pixel value (18).

In a preferred embodiment, the present invention then calls "Update_WL_palette." This palette shows the Window and Level curve. The new window and level parameters are then passed and stored in the database Image structure (19) and the present invention calls "DrawWindow." The DrawWindow function utilizes the window that the user has indicated with a double click or by drawing a rectangle and utilizes these new windowing and leveling values that were stored in the image structure to redraw the entire image (20).

If a ROI rectangle has been created to designate a region of interest within the image (7), a preferred embodiment of the present invention calculates the Point of origin of the mouse and the last point, and saves the parameters in the database image structure (8). The present invention then calls the histogram update function (10) and the histogram calculation function. The original data information determines what parameters are utilized (12) and then the ROI minimum and maximum pixel values are calculated for pixels within the region of interest, and the new values are stored (15).

The present invention reduces the range of pixel data displayed by representing or displaying a range of pixel values which have a minimum value slightly greater than the minimum value of the actual pixel values in the image and a maximum value slightly less than the maximum value of the pixel data in the image. The present invention centers the display range around the values which comprise the majority of the data. The preferred embodiment thus improves the fidelity of the displayed data by not displaying values from the calculation of minimum and maximum pixel values for determining new window and level values for display.

For example, in an x-ray image on film, the clear film surrounding the x-ray image would be scanned in as the color white and represented as a digital pixel value of zero (0) intensity. The blank film is not part of the image, but inappropriately skews the windowing and leveling values for displaying the image. Similarly, there may be black spots on the image which would also skew the windowing and leveling display values. It is desirable to eliminate these minimum white values and maximum black values from the calculation of the new window and leveling values for display.

In the present example, these spurious black and white values comprise a small percentage of the total pixels which represent an image. By removing a small percentage of pixels, the present invention removes spurious data while maintaining necessary data when actual values of interest span the minimum and maximum range. Thus, in a preferred embodiment a small percentage of pixel values are removed from the histogram data set to eliminate spurious pixel values before calculating the window and leveling values for displaying the image. The present invention counts the pixels which represent the image scanned into the PACS. In the present invention this data is utilized to determine the maximum and minimum pixel values. The histogram data already exists in PDS so the histogram data is utilized by the present invention as an expedient means of determining these minimum and maximum displayed values. The histogram data is a count of the number of occurrences for each pixel value in the image. The present invention utilizes the histogram to eliminate spurious pixel values before calculating the new window and level values for display. For example, if the pixel values range from 1000–2000, but there are only a few pixel values at 1000 and many values at 1500, the present invention would ignore the pixel values at 1000 and use a value near 1500 as the minimum pixel value for calculating the window and level values for display. The values at 1000 are actually remapped to the new minimum near 1500.

In a preferred embodiment the present invention sums up the total number of occurrences of all pixel values and determines 1% or some small percentage of the number of occurrences, to arrive at a truncation value N. Thus the present invention is adaptive so that the number of pixel magnitudes that are clipped or truncated are proportional to the mean weight of the data. For example, if the majority of the data have values near the center of the pixel value range, the present invention will clip or truncate a greater range of pixel values. However if the data contains a great deal of white or near zero (0) values and black or near maximum values, the present invention will clip a smaller range of pixel values from the image data before calculating window and level values thus preserving data integrity. The present invention will truncate only one or two pixel values from the maximum and minimum values of the actual pixel data values when the data is spread over the entire magnitude range.

Thus by removing N values from the range of pixel values, in magnitude order, from the low magnitude end, and N values from the high magnitude end of the pixel values, the remaining pixel values are utilized to calculate window and level values so that the image is displayed with improved fidelity because the spurious values have been removed and no longer skew the calculated window and leveling values for displaying the image.

For example, a small image might comprise 100,000 pixels. N or 1% of the total pixels equals 1000. The present invention thus would remove 1000 pixels from the low end and 1000 pixels from the high end of the pixel data and utilize the 1001st value at the low end for the new minimum pixel value and the 1001st pixel value from the high end as the new maximum pixel value. The present invention then calculates the new window and level values utilizing these new minimum and maximum pixel values.

The histogram data comprises a count of pixel magnitude occurrences listed in magnitude order. If there are 1000 (1% or N in the present example) pixel values less than or equal to the pixel value MIN (e.g. 1050), the pixel value MIN or 1050 is designated as the new numerus pixel value for determining new window and level values.

Similarly, if there are 1000 pixel values (1% or N in the present example) greater than or equal to the pixel value MAX (e.g. 1550), the pixel value MAX or 1550 is designated as the new maximum pixel value for determining new window and level values. In other words, the magnitude of the 1001st occurrence of pixel magnitudes from the high end and low end, listed in magnitude order in the histogram data, is selected as the new maximum and new minimum for calculating a new window and level value. All pixels with a magnitude less than MIN (or the 1001st occurrence of a pixel magnitudes, 1050 in the present example) are set equal to MIN or 1050. All pixel values greater than MAX (or the 1001st occurrence of pixel magnitudes) are set equal to MAX or 1550 in the present example.

The new window value equals (MAX−MIN) (1550−1050 in the present example). The new level value equals MIN+ ½(MAX−MIN) or 1050½(1550−1050) in the present example. The pixels are then redrawn, including pixels which were set to MIN or MAX, with improved fidelity and dynamic range.

Dynamic range of a typical display is limited. It is desirable to optimize this limited dynamic range. Typical pixel values range from 0–4095 for 12-bit pixel values. A typical display utilizes 8-bit pixels for output, which limits a display to representing 256 values which range from 0–255. Without limiting the range of pixel values represented on a display, 4096 pixel values ranging from 0–4095 must be represented by 256 display values. Thus each bit of a display value must represent 4096/256 or 16 values from the original image. Thus values which are separated by 16 or less in the original image are mapped to the same bit or value for display. This reduces the dynamic range represented by the display and reduces a physician's ability to see subtle differences on the display which exist in the source image.

By reducing the number of pixel values to include only that range of pixel values which include the majority of the data, the present invention decreases the number of pixel values that must be represented by a single output display bit. Thus, smaller variations in magnitude in the source image are visible on the display.

In the present example, if the minimum pixel value MIN is 1050 and the maximum pixel value MAX is 1550, only the pixel magnitude range from 1050 to 1550 must be mapped to the 256 possible values available at the display. In this case, each display value then represents 500/256 or less than 2 values are mapped to the same bit or value on the display. Thus the dynamic range of the display is improved, the fidelity of the image display is improved, and the physician is better able to detect changes in pixel values which are now separated by only two bits. This example illustrates an improvement factor of 8 (16/2) over typical display techniques by utilizing the present invention.

The present invention, when calculating a ROI image, skips the process of clipping stray pixel values (17) and calculates the window and level values for the new histogram values, passes the rectangle window and level values to the image structure (19), and redraws the entire image, with the region of interest being significantly in fidelity and display dynamic range (20). FIG. 6 illustrates how the defined ROI image appears on a display monitor.

Source Code

In a preferred embodiment, Region of Interest process is programmed as C language functions in a Macintosh environment. Functions that perform logically related tasks are grouped as application modules during program development. A Flowchart illustrating a high level processing flow for the software is shown in FIG. 12.

A detailed source code listing for the modules is contained in the Software Microfiche Appendix. The operations carried out by the source code of preferred embodiment, are self-explanatory to a person of ordinary skill in the art with a working knowledge of the C programming language.

In describing the invention, reference has been made to a preferred embodiment. However, those skilled in the art and familiar with the disclosure of the invention may recognize additions, deletions, substitutions, or other modifications which would fall within the scope of the inventions defined in the claims.

It will be appreciated by those skilled in the art having the benefit of this disclosure that this invention is believed to be capable of application in other situations in which the hardware and software work in substantially the same way to achieve essentially the same result. Some of these situations have been expressly described here (as examples and not as limitations), and others will be recognized by those of skill in the art.

It is also to be understood that various modifications and changes may be made e.g., in the shape, size and arrangement of components, operating steps and so forth, without departing from the spirit and scope of the invention.

Other embodiments of the invention will become apparent to those skilled in the art, from a consideration of this specification or practice of the invention disclosed herein. It is intended that the specification and examples be considered as exemplary, with the true scope and spirit of the invention being indicated by the following claims.

Glossary of Relevant Terms

This glossary defines, discusses, or explains terms as they apply to the present invention. Italicized terms also appear as glossed words. Application developers may use slightly different meanings for some of these terms, but the definitions are given from the user's point of view. Cross-references are given for related or contrasting terms.

| TERM | DEFINITION |
| --- | --- |
| activate | In PDS, to make a program command available for use by means of an appropriate point and click operation. Such operations are interpreted by the event handlers and carried out by the application modules. |
| ACR-NEMA | A "standard" format designed for the interchange of images between different types of equipment. It was formalized by the American College of Radiology (ACR) and national Electrical Manufacturers Association (NEMA). The standard provides for a description of the image display format without having to modify |
| annotate | See image composition |
| bit map | A set of bits that represents the position and state of corresponding items. See pixel. |
| choose (or select) | Pointing and clicking or utilizing a keyboard equivalent to make a choice, such as selecting a command from a menu. |
| click | Move the mouse to position the pointer over a desired item, then press and release the mouse button without moving the mouse. |
| command | A word or phrase, usually in a menu, describing an action for the computer to perform. |
| Configuration file | A data file utilized by the application |

| TERM | DEFINITION |
|------|------------|
| | software to provide information regarding the types of peripheral devices and their physical and mechanical properties. The configuration describes the devices, optional features, system or communication parameters, and the programs installed. |
| Data Acquisition | A system that acquires images from an imaging device and makes them available to the transmission system that transfers the images from one MIG to another. |
| Dedicated device | Typically in proprietary configurations, a dedicated device is specifically configured so that it is solely utilized by its controller. Otherwise, a dedicated device may be a device such as a printer that is utilized only for x-ray film prints. |
| default value | A predetermined attribute, option, or value that is utilized when no other value is explicitly specified. |
| demographic data | Vital statistics for a patient, including name, age, sex, ID number, referring physician, etc. |
| disk | The magnetic medium which the computer uses for storing information. |
| double-click | Position the pointer where the user wants an action to take place. Press and release the mouse button twice in quick succession without moving the mouse. (see click). |
| dragging | Moving an object around the screen as if it were attached to the pointer. Performed by holding the select mouse button and moving the pointer. When a user releases the mouse button, this action confirms a selection or moves an object to a new location. |
| file | A collection of related data stored and retrieved by an assigned name. |
| format | A specific arrangement of a dataset. See protocol. |
| graphics user interface | In modem computer environment, the use of a fairly high resolution video monitor and bit-mapped graphics yields a WYSIWYG (what you see is what you get) appearance to the objects and images represented on the display screen. |
| Header data | Patient demographics information on machine setting, institutional demographics, and director information that enables the image database management system to locate specific images. |
| highlight | To make something visually distinct from its background, usually to show that it has been selected or chosen. |
| IE | Imaging Equipment, the device which creates the original image. |
| Image data | An array of gray-scale values within a digital data element referred to as a pixel (picture element). |
| Image | Images can be captured (acquired from the source modality), stored (locally, or remotely) temporarily or archived for a long period, retrieved from local or remote storage, viewed, previewed, adjusted, manipulated, and composed. |
| industry standard communication format | The medical computing industry has adopted the ACR-NEMA communication sta lowed in formulating messages to include all portions of information that make up its associated demographic data. |
| image palette | One type of pull-down menu. In PDS, the palette that contains the tool icons utiliz sition frames. |
| ITN | Image Transmission Network |
| l | Symbol for Window Center |
| MIG | Medical Imaging Gateway, a Vortech process utilized to route ACR-NEMA mess |
| Medical diagnostic image | In medical applications, images captured on film pages of typical medical images. imaging modalities. |

| TERM | DEFINITION |
|------|------------|
| Modality | Generic term for the various kinds of medical image producing devices; for exam cameras, or ultra-sound. |
| mouse | A type of pointer device moved on a flat surface. As the user moves the mouse, t tance in the same direction. |
| Operating system | A software program that organizes the actions of parts of the computer and its peri level tasks such as memory management, port control, and disk input and output. |
| PACS Picture archival and communication system | In medical applications, a computer based system that permits the user to capture, medical diagnostic images. |
| Parameter | Information supplied by a program or user to an application program. Some applic for "data forms," or information about peripheral devices. |
| PCW | Picture Composite Workshop, a software application utilized on the PDS. Patent |
| PDS | Vortech Data, Inc. personal display station. |
| Pixel | A pixel (picture element). |
| Protocols | In network communication, various sets of standard rules that govern the operation of functional units of a communications system that must be followed if orderly communications are to occur. |
| TCP/IP | Transmission Control Protocol/Internet Protocol |
| Value | A specific occurrence of an attribute; for example, "Sam" for a patient name. A value is the quantity assigned to constants, parameters, variables, or symbols. |
| w | The symbol for Window Width. |
| Workstation | In the present example of a preferred embodiment of the present invention, the computer and monitor. The workstation can be configured on a network with other Vortech systems, such as the IARS (Image Archive and Retrieval System) or MIG (Medical Image Gateway). The workstation can be configured to work with other vendor's systems, such as Eastman Kodak's IMAGELINK. |

We claim:

1. A method for displaying a medical diagnostic image comprising the steps of:

(a) scanning an x-ray film image of a patient into a digital representation of pixels values corresponding to intensity of points on the x-ray film;

(b) displaying the pixels values on a workstation;

(c) selecting an area within the pixel values displayed on the workstation;

(d) calculating a window width equal to difference between MAX and MIN and a window level value equal to the window width divided by 2 plus MIN, for all pixel values displayed.

2. The method of claim 1 further comprising the step of:

calculating a histogram for the selected area representing a number of occurrences of pixel values which occur in selected area.

3. The method of claim 1 further comprising the steps of:

(e) determining a total number of occurrences of all pixel values represented in the histogram which occur in the selected area;

(f) determining a number N equal to a selected percentage of the total number of occurrences of all pixel values which occur in the selected area;

(g) calculating a first sum comprising a number of occurrences of pixel values starting with the smallest pixel value represented in the histogram and preceding to a next smallest pixel value represented in the histogram and continuing to the next smallest pixel value until the total number of occurrences becomes greater than or equal to N;

(h) setting a variable MIN equal to a pixel value represented in the histogram when the first sum becomes greater than or equal to N;

(I) calculating a second sum comprising a number of occurrences of pixel values starting with a number of occurrences of a largest pixel value represented in the histogram and preceding to a number of occurrences of a next largest pixel value occurring in the histogram until the second sum becomes greater than or equal to N; and (j) setting a variable MAX equal to a pixel value represented in the histogram when the second sum of occurrences becomes greater than or equal to N.

4. The method of claim 1 further comprising the steps of:

(e) selecting less than all the pixel values occurring within the selected area; and (f) calculating a histogram based on the selected pixel values representing a number of occurrences of each pixel value which occurs in the selected pixel values.

5. The method of claim 4 further comprising the steps of:

(g) determining a total number of occurrences of all pixel values occurring in the selected area;

(h) determining a number N equal to a selected percentage of a total number of occurrences of all pixel values which occur in the selected area;

(I) calculating a first sum of occurrences for pixel value starting with a smallest pixel value represented in the histogram until the first sum becomes greater than or equal to N;

(j) setting a variable MIN equal to a pixel value represented in the histogram when the first sum becomes greater than or equal to N;

(k) calculating a second sum of a number of occurrences of pixel values starting with a largest pixel value represented in the histogram and preceding to the next largest pixel value represented in the histogram until the second sum becomes greater than or equal to N; and (l) setting a variable MAX equal to a pixel value represented in the histogram when the second sum becomes greater than or equal to N.

6. A method for displaying a medical diagnostic image comprising the steps of:

(a) scanning x-ray film containing a diagnostic image of a patient into a digital representation of pixel values corresponding to intensity values for a particular point n the x-ray film;

(b) displaying the pixel values on a workstation;

(c) selecting an area within the pixel values displayed on the workstation;

(d) calculating a histogram for the selected area representing a number of occurrences of each pixel value which occurs in the selected area;

(e) determining a total number of occurrences of all pixel values which occur in the selected area;

(f) determining a number N equal to a selected percentage of the total number of occurrences of all pixel values which occur in the selected area;

(g) adaptively calculating a first sum comprising a number of occurrences of pixel values starting with a number of occurrences of a smallest pixel value represented in the histogram and preceding to add to the first sum a number of occurrences of a next smallest pixel value represented in the histogram and continuing to a number of occurrences of a next smallest pixel value represented in the histogram until the first sum of occurrences is greater than or equal to N;

(h) setting a variable MIN equal to a pixel value represented in the histogram when the first sum becomes greater than or equal to N;

(I) adaptively calculating a second sum comprising the number of occurrences of pixel values starting with the number of occurrences of a largest pixel value represented in the histogram and preceding to add to the second sum, a number of occurrences of a next largest pixel value represented in the histogram and continuing to a next largest pixel value represented in the histogram until the second sum is greater than or equal to N;

(j) setting a variable MAX equal to a pixel value represented in the histogram at which the second sum becomes greater than or equal to N; and (k) calculating a window width equal to difference between MAX and MIN and a window level value, equal to the window width divided by 2 plus MIN, for all pixel values displayed.

7. The method of claim 1 wherein the percentage selected in step (f) is 1 percent.

8. The method of claim 6 further comprising the step of:

(l) providing a user interface to enable a user to select a region of interest within a set of displayed digital pixel values for calculation of window width and window level values for all pixel values displayed.

* * * * *